United States Patent [19]

Larsonneur

[11] Patent Number: 5,522,809
[45] Date of Patent: *Jun. 4, 1996

[54] ABSORBENT ADULT FITTED BRIEFS AND PADS

[75] Inventor: Lionel M. Larsonneur, Pomona, Calif.

[73] Assignee: Paper-Pak Products, Inc., La Verne, Calif.

[*] Notice: The term of this patent shall not extend beyond the expiration date of Pat. No. 5,252,374.

[21] Appl. No.: 101,229

[22] Filed: Aug. 2, 1993

Related U.S. Application Data

[63] Continuation-in-part of Ser. No. 837,820, Feb. 18, 1992, Pat. No. 5,252,374.

[51] Int. Cl.⁶ ..................................................... A61F 13/15
[52] U.S. Cl. .......................... 604/361; 604/365; 604/368; 604/378; 604/381; 604/384; 604/385.2
[58] Field of Search ....................... 604/358, 361, 604/365, 368, 370, 374–385.2, 389; 428/68, 74, 76–77, 152–154, 184, 156

[56] References Cited

U.S. PATENT DOCUMENTS 3,370,590  2/1968  Hokanson et al. .
3,848,599  11/1974 Schaar .
3,886,941  6/1975  Duane et al. .
3,918,454  11/1975 Korodi et al. ............................ 604/361
4,093,765  6/1978  Schmidt .
4,212,302  7/1980  Karami .................................... 604/374
4,410,324  10/1983 Sabee ...................................... 604/368
4,753,645  6/1988  Johnson .
4,787,896  11/1988 Houghton et al. ....................... 604/340
4,960,477  10/1990 Mesek ..................................... 604/378
5,037,409  8/1991  Chen et al. .............................. 604/358
5,087,506  2/1992  Palumbo et al. ........................ 604/368
5,175,046  12/1992 Nguyen .................................. 604/368
5,197,958  3/1993  Howell .................................. 604/385.1
5,252,374  10/1993 Larsonneur ............................. 604/354

Primary Examiner—Randall L. Green
Assistant Examiner—K. M. Reichle
Attorney, Agent, or Firm—Henry M. Bissell

[57] ABSTRACT

An absorbent pad effectively adapted for use as an adult diaper or, in a slightly different version, to be worn as an absorbent disposable pad within reusable panties. The product includes a liquid impervious backing sheet, a liquid permeable upper facing sheet adhered to the backing sheet about the edges thereof and an intermediate absorbent pad combination comprising upper and lower tissue layers and a paper fluff filler mat sandwiched together with a pair of spatially separated barrier strips that are positioned parallel to each other along the sides of the article between the two tissue layers. The plies of the tissue layers are formed with a crepe-like irregular surface oriented to develop a wicking action directed along the layers in a transverse direction, toward the absorbent barrier strips.

35 Claims, 2 Drawing Sheets

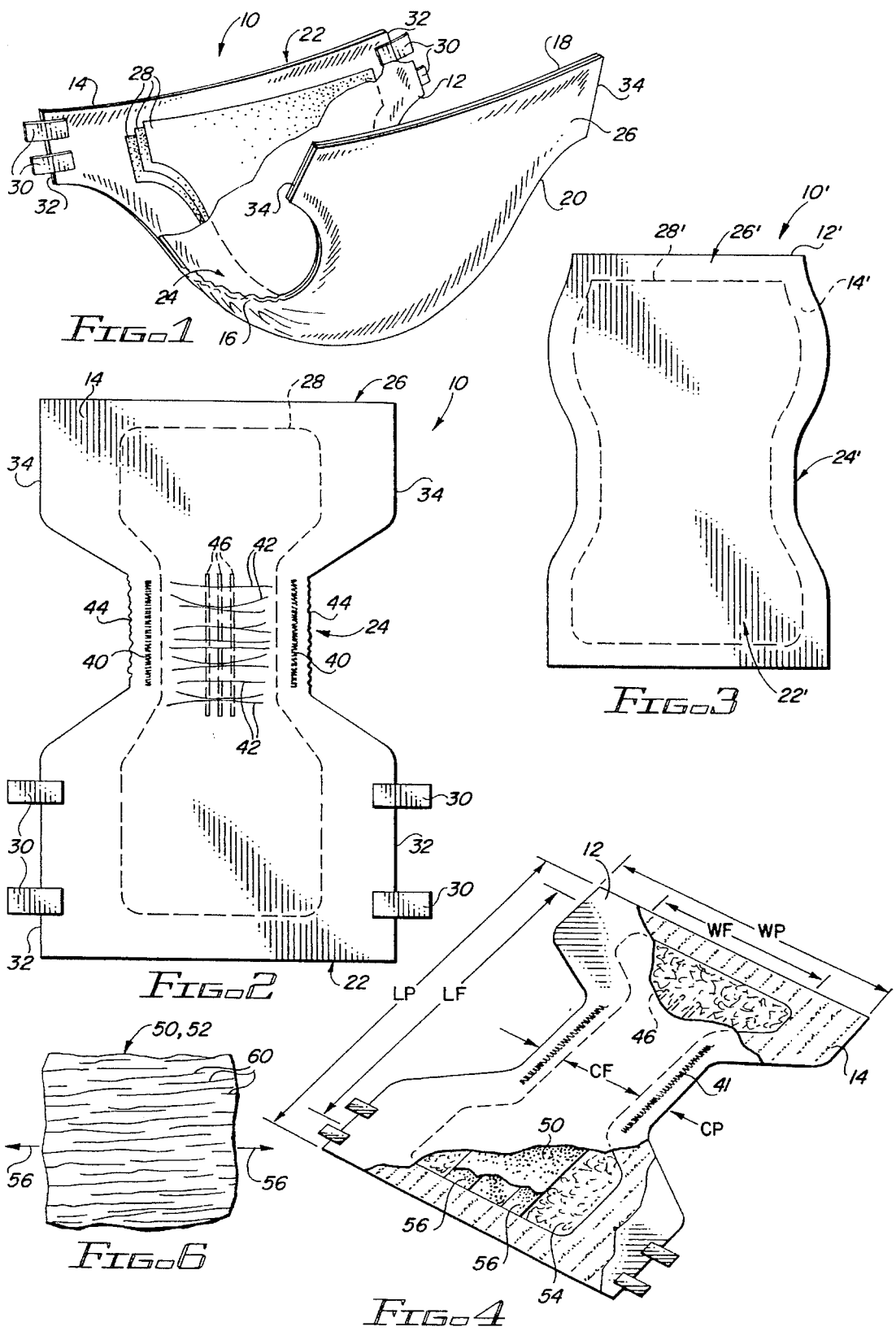

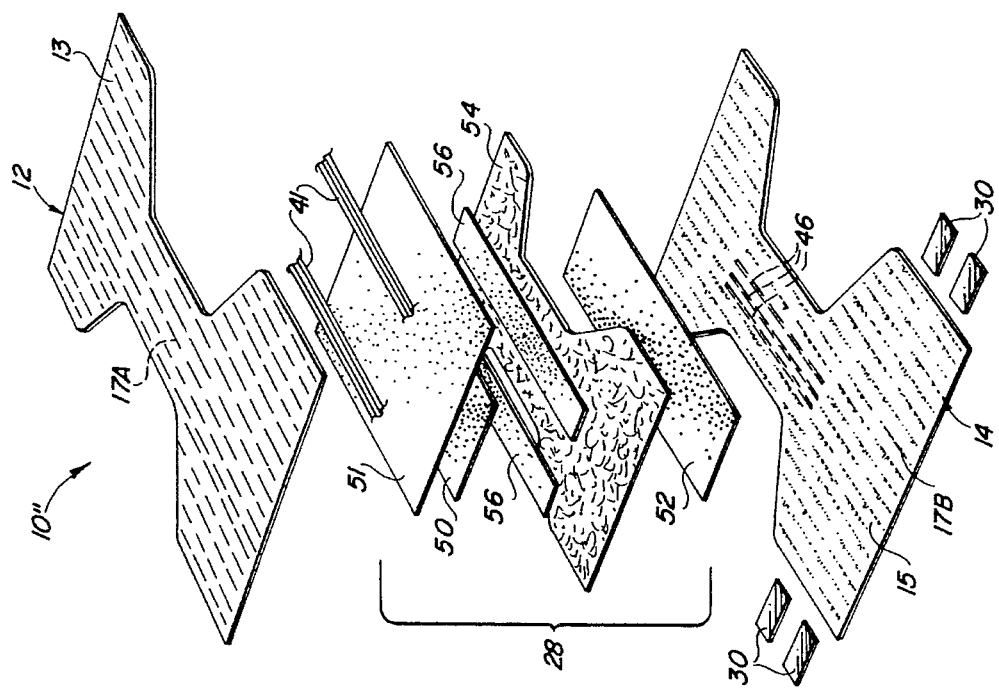
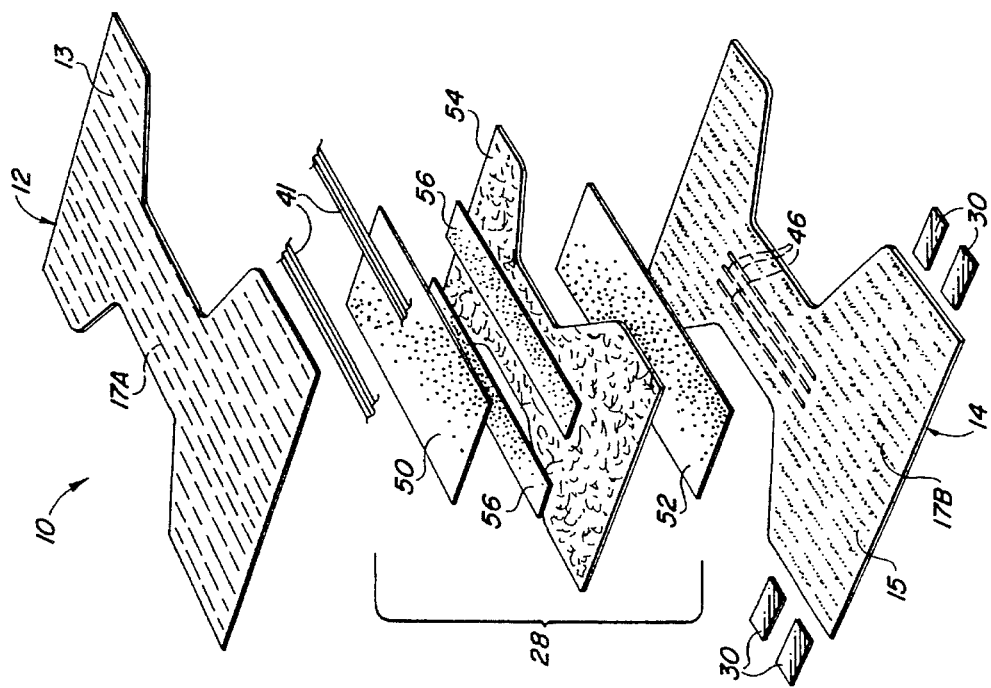

ABSORBENT ADULT FITTED BRIEFS AND PADS

CROSS-REFERENCE TO RELATED APPLICATION

This application is a continuation-in-part of prior application Ser. No. 07/837,820, filed Feb. 18, 1992 now U.S. Pat. No. 5,252,374.

BACKGROUND OF THE INVENTION

1. Field of the Invention

This invention relates to absorbent pads for body fluids and, more particularly, to such pads fabricated as adult fitted briefs (sometimes referred to as "adult diapers") and for wear in panties for adults.

2. Description of the Related Art

Disposable diapers have been known in the art for a number of years and have gained widespread acceptance by consumers, both in private homes and in hospitals and institutions. Their present commercial success is due in part to the elimination of the necessity of storing, washing and folding the disposable diapers as is the case with conventional cotton woven diapers.

To compete with the conventional product, the cost of the disposable diaper must be relatively low and it should be similar to a cloth diaper with regard to absorbency, softness, bulk and conformability. These qualities are particularly important in the case of adult diapers.

With the increasing average age of the senior population, problems with incontinence become more prevalent. Disposable diapers for adults have developed as an important segment of the diaper market, as have also the use of disposable pads with reusable panties. The factor of absorbency, ever important with diapers and disposable pads and inserts for infants, becomes even more critical with respect to diapers for adults. The quantity of urine voided by an adult is likely to be substantially greater than that of an infant and, in addition, in certain nursing homes and other care facilities, the adult patient may not be attended to as assiduously as with a mother looking after her infant.

Various disposable diapers and diaper insert pads are disclosed in the following U.S. Pat. Nos.:

U.S. Pat. No. 3,370,590 of Hokanson et al

U.S. Pat. No. 3,848,599 of Schaar

U.S. Pat. No. 3,886,941 of Duane et al

U.S. Pat. No. 4,093,765 of Schmidt

U.S. Pat. No. 4,753,645 of Johnson.

In the case of bed-ridden patients, absorbent underpads may be used in place of or as an adjunct to adult diapers, principally to provide protection for the bed and bedding in which the patient is confined. In an effort to improve the absorbent capability of hospital underpads, as well as with diapers, variations have been developed in which wood pulp is interspersed with soft fibrous tissue layers. Sometimes, a super-absorbent powder is mixed with the wood pulp in homogeneous distribution within the pad. Unfortunately, if such pads or disposable diapers are left with a patient too long, the filling with liquid develops a slimy combination of the wood pulp, super-absorbent powder and urine that is particularly likely to cause skin breakdown if left in contact with the patient's body. Thus such arrangements, even though more absorbent, still do not provide a completely satisfactory answer to the problem of developing an absorbent pad or diaper for incontinent patients.

A particular construction for hospital underpads which develops an improved capability for liquid absorption by virtue of its novel structural configuration as well as its use of particular absorbent materials has been discovered. This construction of an absorbent underpad for use on beds in hospitals, nursing homes, and the like is disclosed in prior patent application Ser. No. 07/837,820 entitled UNDERPAD FOR INCONTINENT PATIENTS now U.S. Pat. No. 5,252,374. The disclosure of that application is incorporated here by reference as though set out in haec verba. Not only does the construction of such hospital underpad develop increased capacity for absorbing liquid, but its unique fabrication provides an enhanced wicking action which directs liquid away from the central portion of the pad and away from the uppermost layer, leaving the upper layer feeling dry to the touch.

SUMMARY OF THE INVENTION

The novel features of construction of such hospital underpad have been adapted to utilization in adult diapers and disposable inserts for reusable panties. In brief, arrangements in accordance with the invention basically comprise an uppermost layer to be worn next to the skin, a bottom or backing layer remote from the uppermost layer, and a plurality of intermediate layers to establish the liquid absorbent capability of the disposable diaper or pad.

Describing the absorbent pad in particular, the upper layer (or upper facing sheet) of the article is a porous layer, permeable to liquid, of open weave, spun-bonded sheet, hydrophobic material, preferably of polypropylene facing. The open weave has a sufficiently open fiber distribution to render it translucent. It is treated with a surfactant to improve its porosity for liquid. Directly underneath that is a transfer layer of non-woven polyester hydrophilic material or of tissue which allows liquid to pass through readily into the inner layers of the pad but impedes any passage of the liquid in the opposite direction. Next, along the inner side of the transfer layer, is an upper layer of tissue. The upper surface of the transfer layer, being next to the uppermost layer, tends to draw liquid through the open weave. However, the lower surface of the transfer layer, being next to the upper tissue layer, does not exhibit the same tendency, thus accounting for the directional transfer of liquid therethrough.

The upper tissue layer comprises a plurality of plies of thin, soft, fibrous tissue which are formed together to constitute the upper absorbent tissue layer next to the transfer layer. This combination of the one-way liquid passage effected by the transfer layer and the absorbency of the adjacent tissue layer achieves the very beneficial result that the pad develops a feeling of dryness along its upper surface, even though it may have only recently been wet.

Beneath the upper tissue layer and extending lengthwise of the disposable pad is, preferably, a pair of spatially separated strips of laminated super-absorbent polymer powder material. These laminated strips, spaced outward from the center line and extending virtually the full length of the pad, serve as barriers to any liquid which passes by capillary action outward from the central region of the pad. On the under or outer side of these barrier strips is a lower tissue layer, essentially identical to the upper tissue layer. Between the barrier strips and the lower tissue layer is a layer of paper pulp fluff filler, loosely packed, for additional absorbency.

The upper and lower tissue layers are formed of as many as ten plies of highly absorbent tissue, fabricated with a crepe construction which is aligned transversely of the pad to establish a preferential direction for the capillary action for liquid which is absorbed within the tissue layers. Together with the barrier strips and the fluff filler layer between them, the upper and lower tissue layers form a sort of sandwich. The combination of the transversely directed wicking action in conjunction with the super-absorbent barrier strips along the sides of the pad serves to direct the liquid away from the central region of the pad to the barrier strips where the liquid is absorbed. Thus the central region of the disposable pad is kept reasonably dry, even though the pad may have a substantial amount of liquid within it, and the removal of liquid from the center makes the upper facing layer feel dry to the skin.

The barrier strips are of laminated absorbent material, comprising upper and lower thin layers of absorbent tissue with super-absorbent powder distributed in a generally random fashion between them. These barrier strips are available commercially from Gelock, Inc., Pine Lake Industrial Park, Dunbridge, Ohio 43414.

Adult diapers in accordance with the present invention incorporate a disposable absorbent pad such as that which is described immediately hereinabove. The diaper is formed with an extended skirt area projecting laterally from both opposite ends of the pad sufficient to permit encirclement of the waist of the wearer. Adhesive tabs are mounted to the projecting skirt portions at strategic points to provide for the fastening of the adult diaper in place on the wearer. Elasticized stitching is incorporated in and along the side edges of the pad approximately equidistant from the opposite ends to facilitate placement of the pad on the wearer. The elasticized stitching is in the crotch region and helps to maintain the diaper, particularly the side edges thereof located in the crotch region, in close proximity to the skin of the wearer while serving to prevent leakage in the immediate location where urine is deposited in the pad until the wicking action achieved by the barrier strips can serve to distribute the liquid throughout the diaper pad.

Along the outer side of the pad, generally in the crotch region extending longitudinally and located between the elasticized stitching on the side edges, is a plurality—for example, three—of spaced-apart lines of wetness indicators. These comprise a deposit of a particular material having the property of turning a brilliant distinctive color when wet. Thus, a nurse or other attendant can readily tell if the disposable diaper needs changing, simply by observing the color of the indicator lines, without having to feel the diaper for dampness. This material is produced by the H. B. Fuller Company, 1200 W. County Road E, Arden Hills, Minn. 55112 under Product Code No. HL1339X.

BRIEF DESCRIPTION OF THE DRAWING

A better understanding of the present invention may be realized from a consideration of the following detailed description, taken in conjunction with the accompanying drawing, in which:

FIG. 1 is a schematic representation, partially broken away, of a diaper or fitted brief in accordance with the invention;

FIG. 2 is a plan view from the underside of the adult diaper of FIG. 1;

FIG. 3 is a plan view of an absorbent pad in accordance with the invention for wearing inside panties;

FIG. 4 is a perspective view, partially broken away, of the adult diaper of FIG. 1;

FIG. 5 is an exploded view of the adult diaper of FIG. 1;

FIG. 6 is an enlarged schematic representation of a portion of particular elements shown in FIG. 5; and FIG. 7 is a view like FIG. 5 showing a minor modification thereof.

DESCRIPTION OF THE PREFERRED EMBODIMENTS

As represented in the schematic view of FIG. 1, an article 10 in the form of an adult diaper or fitted brief is shown having an inner or upper layer 12 and an outer or lower layer 14 which are adhesively attached to each other about the periphery of the diaper, as along the edges 16, 18 and 20. The article includes a back portion 22, a crotch portion 24 and a front portion 26. Two pairs of peel tapes 30 are respectively mounted at opposite edges 32 of the back portion 22. Between the inner and outer layers 12, 14 are a plurality of layers 28 which are of lesser dimension than the layers 12 and 14 so that they do not extend all the way to the outer edges such as 16, 18 and 20 of the article.

When placed in position on a wearer, the back 22 of the article 10 extends about the back of the wearer, the crotch portion 24 extends forward between the wearer's legs and the front portion 26 is brought up across the waist. When positioned in this manner, edges 32 of the rear portion are brought forward around the sides of the wearer to overlap the side edges 34 of the front portion 26 and the adhesive peel tapes 30 are adhesively affixed to the side edges of the front portion 26, thus holding the garment in position on the wearer's body.

In the plan view of FIG. 2, article 10 of FIG. 1 is shown as viewed from the underside thereof. The lower layer 14 is translucent, as is the upper layer 12, so that the outline of the inner layers 28 is readily discernible from the outside. In the crotch region 24, the material of the diaper is gathered by stitched elastic sections 40 in the peripheral edge regions on either side of the intermediate layers 28. This produces a gathering of the intermediate layers 28 represented by the lines 42. Similarly, the gathering or pleating of the outer layers 12, 14 is represented by the zig-zag lines 44.

Three rows 46 of indicator material are centrally located in the crotch region 24. This material is installed on the inner side of the outer layer 14 but is readily visible through the layer.

FIG. 3 schematically represents an absorbent pad 10' constructed essentially like the absorbent pad portion of the adult diaper of FIGS. 1 and 2, except that it is smaller in size so that it can be worn as a disposable item inside a pair of reusable panties. As such, the pad 10' includes a plurality of intermediate layers 28' between an inner layer 12' and an outer layer 14'. It is shaped to provide a rear portion 22', a crotch portion 24' and a front portion 26'.

As shown in more detail in the partially broken away view of FIG. 4 and the exploded view of FIG. 5, the upper layer 12 comprises a spun-bonded polypropylene cover 13 with lines 17A of adhesive on the underside thereof for final assembly. Polyester elastic thread 41 is shown which establishes the elastic thread segments 40 in the finished article (shown in FIG. 2). The outer layer 14 comprises a polyethylene backing 15 which is impervious to liquid. The outer layer 14 has a plurality of lines of adhesive 17B on the upper side thereof for sealing the completed unit together. The wetness indicator lines 46 are shown along the upper side of the outer layer 14.

The intermediate layers 28 are shown as comprising a top tissue layer 50, a bottom tissue layer 52, a fluff filler pad 54 and two super-absorbent laminant strips 56.

The laminant strips 56 are formed of laminated absorbent material and comprise upper and lower thin layers of absorbent tissue with super-absorbent powder distributed in a generally random fashion between them. These strips 56 are the principal collection elements for liquid deposited in the diaper 10, together with the paper pulp fluff filler mat 54, and serve as barriers to the migration of liquid in an outward direction beyond the strips.

The polypropylene cover layer 13 is a porous layer, readily permeable to liquid, of open weave, spun-bonded sheet which permits any liquid deposited thereon to pass readily into the absorbent intermediate layers 28. The top and bottom tissue layers 50, 52 each comprise a plurality of plies, preferably between 8 and 16, of thin, soft, fibrous tissue. These tissue plies are formed with a crepe construction and the tissue layers are oriented so that the creped surface irregularities are aligned transversely of the absorbent pad; i.e., extending from side-to-side. This alignment of the crepe irregularities establishes the preferential direction for the capillary action of liquid which is absorbed within the tissue layers, thereby enhancing the effect of the capillary action by developing preferential channels to the super-absorbent laminant strips 56. In addition to the super-absorbent laminant strips 56, the paper pulp fluff filler insert 54 provides added liquid-absorbent capacity to ensure effectiveness of the adult diaper 10.

The peel tapes 30 are provided with release layers which are removed prior to use, thereby protecting the adhesive tapes during storage. The adhesive on the peel tapes 30 is releasable so that the diaper 10 can be removed and reinstalled in the event no liquid is deposited during an initial wearing.

FIG. 6 represents a segment of the top and bottom tissue layers 50, 52, enlarged to show the alignment of the crepe line irregularities 60 which are oriented to extend from side-to-side between the barrier strips 56 which are installed outboard to the right and left sides of the tissue layers 50, 52 as depicted in FIG. 6.

FIG. 7 is an exploded view identical to FIG. 5 with the exception that the adult diaper 10" of FIG. 7 includes an additional element in the form of a transfer layer 51 positioned above the upper tissue layer 50. The transfer layer 51 may be fabricated of either tissue or a non-woven material. The addition of the transfer layer 51 develops a certain directionality in the transfer of liquid into the diaper. This phenomenon results from the fact that the upper surface of the transfer layer, being next to the uppermost, permeable layer, tends to draw liquid through the open weave of the polypropylene facing layer. However, the lower surface of the transfer layer 51, being next to the upper tissue layer, does not exhibit the same tendency.

The absorbent pad 10' of FIG. 3 is constructed in the same fashion as the adult diaper 10, described in detail hereinabove, except for the elastic thread portions 40, the wetness indicators 46 and the peel tapes 30. It has the same top and bottom tissue layers 52, the fluff filler layer 54 and the super-absorbent laminant strips 56 sealed between the upper spun-bond, liquid-permeable, polypropylene upper layer 12' and the liquid-impermeable polyethylene backing layer 14. In a variant like FIG. 7, it may also include a transfer layer 51.

The adult diapers are provided in different sizes for small, medium and large users. Width dimensions are indicated in the following Table by reference to the length (L), width (W) and crotch (C) dimensions indicated in FIG. 4.

TABLE

|  | Small | Medium | Large |
| --- | --- | --- | --- |
| Overall size, WP × LP | 17½" × 26¾" | 25¾" × 31¾" | 31½" × 38½" |
| Filler size, WF × LF | 11½" × 22½" | 14½" × 27" | 16½" × 33¼" |
| Crotch, Pad CP | 10" | 12" | 12" |
| Filler CF | 5" | 6" | 6½" |

The embodiments of the present invention as shown and described hereinabove provide a very effective liquid absorbent product for use by adult incontinents. Whether an adult diaper or absorbent pad for wearing with reusable panties, the product is a super-absorbent article which has the capacity for absorbing a large quantity of liquid and storing it away from the user's body. The inner layer of the product has a soft spun-bonded polypropylene sheet which very soon after liquid is deposited thereon feels dry and comfortable to the skin because of its porosity and the effectiveness of the absorbent layers below the top sheet in drawing away the moisture to the storage provided by the paper fluff filler pad and the super-absorbent laminant strips. The outer layer is tear resistant and is impermeable to liquid, thereby serving to contain liquid within the absorbent element region. In the case of the adult diaper, the wetness indicator lines provide a readily apparent indicator to show when the diaper needs changing.

Although there have been described hereinabove various specific arrangements of absorbent adult fitted briefs and pads therefor in accordance with the invention for the purpose of illustrating the manner in which the invention may be used to advantage, it will be appreciated that the invention is not limited thereto. Accordingly, any and all modifications, variations or equivalent arrangements which may occur to those skilled in the art should be considered to be within the scope of the invention as defined in the annexed claims.

What is claimed is:

1. An absorbent article to be worn by incontinent adults comprising:

a backing sheet which is substantially impervious to liquid;

an upper facing sheet which is permeable to liquid;

means for adhering the upper facing sheet and the backing sheet together at edges about the periphery thereof;

a liquid absorbent pad between the facing sheet and the backing sheet for absorbing liquid which may be deposited on the facing sheet; said liquid absorbent pad having a central region generally midway between opposite side edges of the pad, the pad including upper and lower tissue layers respectively adjacent the upper facing sheet and the backing sheet, and a plurality of spatially separated barrier strips situated between the tissue layers and extending generally parallel to the side edges of the pad, said strips being displaced from the central region of the pad;

each of the upper and lower tissue layers comprising a plurality of individual plies of highly absorbent tissue formed with creped surface irregularities which are oriented in a transverse direction of the absorbent pad.

2. The article of claim 1 further including a layer of paper fluff filler material positioned between the two barrier strips and the lower tissue layer for providing additional liquid absorbent capacity to the article.

3. The article of claim 2 further including a transfer layer positioned between the facing sheet and the liquid absorbent pad to facilitate the transfer of liquid into the liquid absorbent pad while inhibiting the flow of liquid in the reverse direction.

4. The article of claim 1 wherein the barrier strips are formed of laminated tissue layers having clumps of super-absorbent polymer powder distributed therein.

5. The article of claim 4 wherein the barrier strips are laminates of thin layers of tissue adhered together.

6. The article of claim 1 wherein the upper facing sheet is formed of spun-bonded polypropylene with a sufficiently open fiber distribution to render it translucent.

7. The article of claim 6 wherein the upper facing sheet is treated with a surfactant to improve its porosity for liquid.

8. The article of claim 1 wherein the backing sheet is formed of a continuous sheet of polyethylene plastic.

9. The article of claim 1 wherein the surface irregularities of the tissue layers are oriented orthogonal to the barrier strips.

10. The article of claim 1 wherein the adhering means comprise a plurality of glue lines extending along adjacent surfaces of the facing and backing sheets.

11. The article of claim 10 configured to form front and back portions joined by a crotch portion which is narrower than the front and back portions, said article being provided for wearing by an incontinent adult inside a pair of reusable panties.

12. The article of claim 1 wherein the facing and backing sheets are formed with extended side sections at opposing front and back portions thereof on opposite ends of a narrowed crotch portion to constitute an adult diaper.

13. The article of claim 12 further including a plurality of releasable adhesive members affixed to the side edges of the back portion for attachment to corresponding side edges of the front portion when the article is installed in position about a wearer.

14. The article of claim 13 further including elastically stitched elements extending longitudinally in the crotch portion adjacent opposite side edges thereof.

15. The article of claim 14 further including at least one wetness indicator element having the property of changing its visual appearance when liquid is applied thereto.

16. The article of claim 15 wherein said at least one wetness indicator has the property of changing color when wet.

17. The article of claim 16 wherein said at least one wetness indicator comprises a line of liquid sensing material.

18. The article of claim 15 wherein said at least one wetness indicator comprises a plurality of lines of liquid sensing material mounted along the inner surface of the backing sheet and visible therethrough.

19. The article of claim 18 wherein said wetness indicator lines are aligned generally longitudinally of the article and centrally located in the vicinity of the crotch portion.

20. An absorbent article for wearing by an incontinent adult comprising:

a plurality of absorbent tissue layers sandwiched between, and sealed within an envelope defined by, an impervious backing layer and a liquid permeable upper facing layer, the edges of the backing layer and the facing layer being adhered together about the periphery of the article, said article including a longitudinal center region approximately midway between opposed side edges of the article;

a plurality of generally parallel barrier strips situated between upper and lower tissue layers, said strips being oriented generally parallel to the side edges of the article and positioned on opposite sides of the center region and spaced from said side edges;

said plurality of tissue layers comprising an upper tissue layer and a lower tissue layer respectively above and below said barrier strips, each of said tissue layers comprising a plurality of plies of highly absorbent tissue fabricated to provide a selectively directed capillary action for liquid absorbed therein; and means for selectively orienting the direction of capillary action provided by said tissue layer plies, said means comprising creped tissue plies with the crepe direction oriented transversely of the article.

21. The article of claim 20 further comprising a paper fluff filler mat positioned between the lower tissue layer and said barrier strips, said fluff filler mat providing added liquid absorbent capacity to that of the barrier strips.

22. The article of claim 21 further including a transfer layer positioned between the facing layer and the plurality of absorbent tissue layers to facilitate the transfer of liquid into the absorbent tissue layers while inhibiting the flow of liquid in the reverse direction.

23. The article of claim 22 wherein said barrier strips are two in number, each being formed of laminated tissue layers with clumps of super-absorbent powder distributed therein.

24. The article of claim 23 wherein each of said strips comprises a pair of thin absorbent tissue layers with the clumps of super-absorbent powder scattered throughout the strip and held between the layers.

25. The article of claim 22 further including adhering means in the form of a plurality of glue lines extending along adjacent surfaces of the facing and backing layers.

26. The article of claim 25 configured to form front and back portions joined by a crotch portion which is narrower than the front and back portions, said article being provided for wearing by an incontinent adult inside a pair of reusable panties.

27. The article of claim 20 wherein the direction of capillary action is from the center of the article outward toward the barrier strips and from the side edges inward toward the barrier strips.

28. The article of claim 20 wherein the facing and backing layers are formed with extended side edges at opposing front and back portions thereof on opposite ends of a narrowed crotch portion to constitute an adult diaper.

29. The article of claim 28 further including a plurality of releasable adhesive members affixed to the side edges of the back portion for attachment to corresponding side edges of the front portion when the article is installed in position about a wearer's body.

30. The article of claim 29 further including elastically stitched elements extending longitudinally in the crotch portion adjacent opposite side edges thereof.

31. The article of claim 30 further including at least one wetness indicator element having the property of changing its visual appearance when liquid is applied thereto.

32. The article of claim 33 wherein said at least one wetness indicator has the property of changing color when wet.

33. The article of claim 32 wherein said at least one wetness indicator comprises a line of liquid sensing material.

34. The article of claim 32 wherein said at least one wetness indicator comprises a plurality of lines of liquid sensing material mounted along the inner surface of the backing sheet and visible therethrough.

35. The article of claim 34 wherein said wetness indicator lines are aligned generally longitudinally of the article and centrally located in the vicinity of the crotch portion.

* * * * *